United States Patent
Breviglieri et al.

(10) Patent No.: US 6,790,986 B1
(45) Date of Patent: Sep. 14, 2004

(54) PROCESS FOR THE PREPARATION OF GABAPENTIN FREE FROM INORGANIC ACIDS ANIONS

(75) Inventors: Gabriele Breviglieri, Treviglio (IT); Sergio Contrini, Treviglio (IT); Cinzia Assanelli, Treviglio (IT)

(73) Assignee: Farchemia S.r.l., Treviglio (IT)

( * ) Notice: Subject to any disclaimer, the term of this patent is extended or adjusted under 35 U.S.C. 154(b) by 0 days.

(21) Appl. No.: 10/445,676

(22) Filed: May 27, 2003

(30) Foreign Application Priority Data

Apr. 18, 2003 (IT) ..................................... MI2003A0825

(51) Int. Cl.[7] ........................ C07C 61/10; A61K 31/195
(52) U.S. Cl. ........................................ 562/507; 514/561
(58) Field of Search ........................... 514/561; 562/507

(56) References Cited

U.S. PATENT DOCUMENTS 6,054,482 A * 4/2000 Augart et al. ............... 514/561

* cited by examiner

*Primary Examiner*—Ba K. Trinh
*Assistant Examiner*—Taylor V. Oh
(74) *Attorney, Agent, or Firm*—Walter H. Schneider

(57) ABSTRACT

Gabapentin free from mineral acids anions is obtained by precipitating from a gabapentin aqueous solution a corresponding hydroxybenzoate, from which pure gabapentin is subsequently obtained by dissolution in a lower alcohol and treatment with a tertiary base.

12 Claims, No Drawings

PROCESS FOR THE PREPARATION OF GABAPENTIN FREE FROM INORGANIC ACIDS ANIONS

The present invention relates to a process for the preparation of gabapentin (1-(aminomethyl)-cyclohexaneacetic acid) of formula

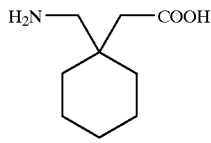

free from inorganic ions, in particular chlorides, and from the corresponding lactam.

TECHNOLOGICAL BACKGROUND

A number of processes for the preparation and/or purification of gabapentin are known: see, for instance, U.S. Pat. Nos. 4,024,175; 5,068,413; 5,091,567; 5,132,451; 5,319,135; 5,362,883; 6,054,482; 6,531,509. The latter two, in particular, respectively concern a process for the preparation gabapentin containing less than 0.5% by weight of lactam and less than 20 ppm of a mineral acid anion (in particular chlorides) and pharmaceutical compositions of gabapentin containing less than 0.5% by weight of lactam and more than 20 ppm of a mineral acid anion (in particular chlorides). According to U.S. Pat. No. 6,054,482, the presence of chlorides in amounts above 20 ppm promotes the conversion of gabapentin into lactam (having some toxicity), which conversion, according to the same Patent, is prevented or slowed down not only by the low content in chlorides, but also by the presence of a number of adjuvants in the corresponding pharmaceutical compositions. On the other hand, according to U.S. Pat. No. 6,531,509 the presence of adjuvants, which are partly the same as those claimed in U.S. Pat. No. 6,054,482, in the compositions would be sufficient for the purpose.

Numerous processes for reducing the chloride ions content in gabapentin exist. For example, aqueous solutions of gabapentin (which is known to be highly water-soluble) are passed through ion exchange columns; or solutions of the corresponding hydrochloride are treated with bases in solvents in which gabapentin is soluble, while the base hydrochloride of is not, or, vice versa, in a solvent wherein the base hydrochloride is soluble whereas gabapentin is not. In each case, according to U.S. Pat. No. 6,054,482 gabapentin completely free from chloride ions cannot be obtained. In this connection, the Patent reads: "The active materials of formula (I) must be prepared as highly purified, nonderivatized free amino acids, for example, from the corresponding hydrochloride by ion exchange. The proportion of remaining hydrochloride admixtures should thereby not exceed 20 ppm. The same also applies to other mineral acids."

SUMMARY OF THE INVENTION

It has now been found that gabapentin completely free from chloride ions (or, more generally, from mineral acids ion) can be obtained from a gabapentin aqueous solution by treatment with a hydroxybenzoic acid (optionally substituted in the ring with lower alkyl or alkoxy groups), preferably with 4-hydroxybenzoic acid and most preferably with salicylic acid. It has in fact been found that the water-solubility of gabapentin 4-hydroxybenzoate, and that of the salicylate even more, is so poor as to obtain its precipitation in satisfactory yields, and that treatment of the solutions of said salts in solvents wherein gabapentin is insoluble or sparingly soluble with suitable organic bases provides precipitation of highly pure gabapentin, containing less 100 ppm of the hydroxybenzoic acid used, while the hydroxybenzoates of said organic bases remain in solution. Furthermore it has been found that the resulting gabapentin, if necessary after stirring with alcohols, substantially contains no lactam. Moreover, in the corresponding pharmaceutical formulations no substantial increases in said content are observed after one-year storage at 25° C. and 60% humidity.

DETAILED DISCLOSURE OF THE INVENTION

According to the invention, an aqueous solution containing approx. 10 to approx. 18 kg, preferably 13–15 kg, of gabapentin per 100 liters of water, at a temperature ranging from approx. 25 to approx. 60° C., preferably from 30 to 45° C., is added with the hydroxyacid in amounts of 0.95–1.05 mols per mol of gabapentin, the preferred molar ratio between the compounds being 1:1. The resulting suspension is stirred at the same temperature for 5–10 hours, then cooled to approx. 15–25° C. The resulting gabapentin hydroxybenzoate is dried under vacuum at approx. 50° C. The yield is approx. 90% on theoretical, with a assay higher than 99.5%. The resulting salt is suspended in a lower alcohol, preferably absolute ethanol, in amounts of approx. 3–5 liters per kg of salt, at a temperature of 15–25° C., and the suspension is added with an amount of tertiary amine (preferably tributylamine and most preferably N-ethyl-diisopropylamine ("Hünig base")) in amounts of 1–1.2 mols per mol of gabapentin hydroxybenzoate. After stirring for some hours at the same temperature, the mixture is cooled to 5–10° C., the precipitated gabapentin is filtered or centrifuged, washed with the same alcohol, then stirred with ethanol containing approx. 10% by volume of water. The suspension is heated for 10–20 minutes at approx. 40° C., left to stand for some hours at room temperature, then left for some hours at −5 to +5° C. and centrifuged, thereby reducing the hydroxyacid content in the final gabapentin to less than 100 ppm; the content in lactam is substantially zero, and does not undergo substantial increases after one year at 25° C. and 50% humidity.

The following examples further illustrate the invention.

EXAMPLE 1

A solution of 20 kg of gabapentin in 140 liters of water is heated at 40° C. and added with 16.1 kg of salicylic acid. The suspension is stirred for 6 hours at 40° C., then cooled to 20° C., centrifuged and dried under vacuum at approx. 50° C. 34.5 kg (95.5% on theoretical) of 99.65% gabapentin salicylate are obtained, melting point 116° C. The elemental analysis (found C, 62.28%; H, 7.53%; N, 4.44%; calculated C, 62.12%; H, 7.49%; N, 4.53%) confirms the nature of the salt, which is suspended in 130 liters of absolute ethanol at 20° C., added with 15.9 kg of N-ethyl-diisopropylamine, then stirred at 20° C. for four hours, cooled to 8–10° C. and centrifuged, washing in centrifuge with approx. 20 liters of absolute ethanol. Drying affords 15.4 kg of gabapentin (86.68% yield), which can be further purified by suspension in 400 liters of ethanol containing 10% by weight of water and heating for some minutes, under stirring, at approx. 40° C. After standing at room temperature for four-five hours, the mixture is cooled to 0° C. and after, a further 4–5 hours at this temperature, is centrifuged and dried. The resulting pure gabapentin (87% yield) has content in salicylic acid lower than 100 ppm and in lactam lower than 0.1%.

EXAMPLE 2

Following the procedure of Example 1, from 1 kg of gabapentin are obtained 1.7 kg (94.1% on theoretical) of gabapentin 4-hydroxybenzoate, m.p. 142.5–142.8° C., with potentiometric assay 99.8%. The elemental analysis (found C, 62.08%; H, 7.57%; N, 4.39%) confirms the nature of the product. Work-up to gabapentin containing less than 100 ppm of 4-hydroxybenzoic acid and less than 0.1% of lactam is carried out as in Example 1.

What is claimed is:

1. A process for the preparation of gabapentin free from inorganic acids anions and from the corresponding lactam, characterized in that a gabapentin aqueous solution is treated with a hydroxybenzoic acid, optionally substituted in the ring with lower alkyl or alkoxy groups, and that the precipitated gabapentin hydroxybenzoate is dried, suspended in a lower alcohol and added with a tertiary base to precipitate pure gabapentin.

2. A process for the preparation of gabapentin free from inorganic acids anions and from the corresponding lactam, characterized in that:
   a) a solution of 13–15 kg of gabapentin in 100 liters of water, at approx. 40° C., is treated with an equimolar amount of salicylic acid;
   b) the resulting suspension is stirred for 5–10 hours at the same temperature and the precipitated gabapentin salicylate is recovered and dried;
   c) said salicylate is suspended in 3–5 liters of absolute ethanol, at 15–25° C., added with N-ethyl-diisopropylamine in amounts of 1–1.2 mols per mol of salicylate, the suspension is stirred for some hours at the same temperature, then cooled at 8–10° C. and gabapentin is recovered by filtration or centrifugation;
   d) optionally, the resulting gabapentin is further purified by re-suspension in approx. 25 parts by volume of ethanol containing 10% of water, stirring for some minutes at approx. 40° C., cooling to approx. 0° C. and final recovery.

3. A process according to claim 1 in which the gabapentin aqueous solution is treated at 25 to 60° C. with 0.95–1.05 mols of hydrobenxoic acid per mol of gabapentin.

4. A process according to claim 1 in which the gabapentin hydroxybenzoate is suspended in about 3–5 liters of a lower alcohol per kg. of gabapentin hydroxybenzoate.

5. A process according to claim 1 in which the lower alcohol is absolute ethanol.

6. A process according to claim 1 in which the gabapentin hydroxybenzoate suspension is treated with 1–1.2 mols of N-ethyl-diisopropylamine per mol of gabapentin hydroxybenzoate at 15–25° C.

7. A process according to claim 1 in which the hydroxybenzoic acid is salicylic acid.

8. A process according to claim 1 in which the hydroxybenzoic acid is 4-hydroxybenzoic acid.

9. A process according to claim 1 in which the resulting gabapentin is purified by stirring its suspension in ethanol containing about 10% water at about −5.0 to +5.0° C. and recovering gabapentin by filtration or centrifugation.

10. A process according to claim 2 in which 4-hydroxbenzoic acid is used instead of salicylic acid.

11. A gabapentin hydroxybenzoate produced according to claim 1.

12. A gabapentin hydroxybenzoate according to claim 11 selected from gabapentin salicylate and gabapentin 4-hydroxy-benzoate.

* * * * *